| United States Patent [19] | [11] | 4,097,609 |
|---|---|---|
| Barcza et al. | [45] | Jun. 27, 1978 |

[54] 2,4-DISUBSTITUTED-4b,5,6,7,8,8a,9,10-OCTAHYDRO-9-OXO-PHENANTHRENES

[75] Inventors: Sandor Barcza, West Orange, N.J.; James B. Hendrickson, Cambridge, Mass.

[73] Assignee: Sandoz, Inc., E. Hanover, N.J.

[21] Appl. No.: 773,535

[22] Filed: Mar. 2, 1977

Related U.S. Application Data

[60] Division of Ser. No. 637,718, Dec. 4, 1975, Pat. No. 4,034,045, which is a continuation-in-part of Ser. No. 566,759, Apr. 10, 1975, abandoned, which is a continuation of Ser. No. 368,939, Jun. 11, 1973, abandoned.

[51] Int. Cl.² .................... C07C 49/82; A01N 9/24
[52] U.S. Cl. ............................ 424/331; 260/590 FA
[58] Field of Search ................ 260/590 FA; 424/331

[56] References Cited

U.S. PATENT DOCUMENTS

| 3,471,565 | 10/1969 | Nagata et al. | 260/590 FB |
| 3,681,427 | 8/1972 | Edwards et al. | 260/590 FB |

OTHER PUBLICATIONS

Fieser et al., Reagents for Organic Synthesis, pp. 293–295 (1965).
Hickenbottom, Reactions of Organic Compounds, pp. 110–117, (1957).
Wagner et al., Synth. Org. Chem., pp. 226–229 & 248–251, (1953).

*Primary Examiner*—James O. Thomas, Jr.
*Assistant Examiner*—James H. Reamer
*Attorney, Agent, or Firm*—Gerald D. Sharkin; Robert S. Honor; Timothy G. Rothwell

[57] ABSTRACT

2,4-Disubstituted-4b,5,6,7,8,8a,9,10-octahydro-9-oxo-phenanthrenes e.g., 2,4-dimethoxy-4b,5,6,7,8,8a,9,10-octahydro-9-oxo-phenanthrene are useful as hypolipidemic agents.

5 Claims, No Drawings

2,4-DISUBSTITUTED-4B,5,6,7,8,8a,9,10-OCTAHYDRO-9-OXO-PHENANTHRENES

This a division of application Ser. No. 637,718 filed Dec. 4, 1975 now U.S. Pat. No. 4,034,045 which is turn is a continuation-in-part of copending application Serial No. 556,759 filed April 10, 1975, now abandoned which in turn is a continuation of application Serial No. 368,939 filed June 11, 1973, now abandoned.

This invention relates to 2,4-substituted-4b,5,6,7,8,8a, 9,10-octahydro-9-oxo-phenanthrene derivatives, intermediates and processes for their preparation and their use as hypolipidemic agents. The compounds of this invention may be represented by the following structural formula:

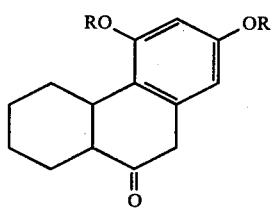

where R represents hydrogen, or lower alkyl, i.e. alkyl having 1 to 4 carbon atoms, e.g., methyl, ethyl, isopropyl and the like.

The compounds of formula (I) in which R is lower alkyl may be prepared by the following reaction scheme:

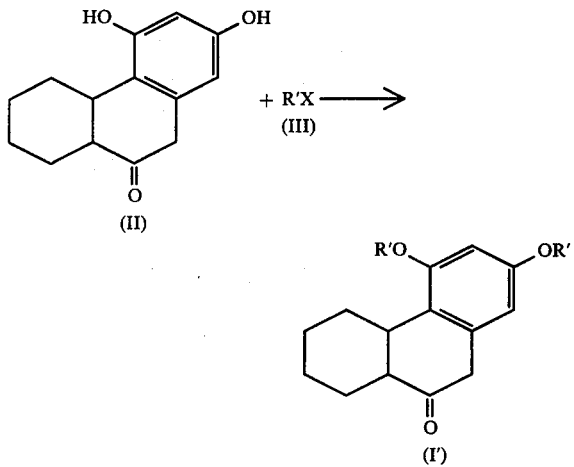

where
X is a leaving group such as chloride, bromide, iodide, methyl sulfate or sulfate, preferably iodide, methyl sulfate or sulfate, and
R' is lower alkyl as defined above.

The compounds of formula (I') are prepared by treating the compound of the formula (II) with a compound of the formula (III) under an inert atmosphere such as argon, neon, nitrogen and the like, preferably nitrogen, in the presence of an acid binding agent and an inert non-aqueous solvent. The particular acid binding agent employed is not critical, although it is preferred that the reaction be carried out in the presence of an inorganic acid binding agent, such as an alkali metal carbonate, e.g. potassium carbonate, sodium carbonate or lithium carbonate, an alkali metal hydride, e.g. sodium hydride, potassium hydride and the like, an alkali metal hydroxide, e.g. sodium hydroxide, potassium hydroxide and the like, or an alkali earth metal hydride, e.g. calcium hydride, especially preferred is potassium carbonate. The acid binding agent employed may also be an organic acid binding agent such as a tertiary amine, e.g. triethylamine. The particular non-aqueous solvent used is not critical, but it is preferred that the reaction be run in the presence of dioxane, tetrahydrofuran, or acetone, the latter being especially preferred. The temperature of the reaction is not critical, but it is preferred that the reaction be carried out between 0° and 150° C., especially the reflux temperature of the solvent. The reaction is run from about 1 to 50 hours, preferably from about 16 to 28 hours. The product is recovered using conventional techniques e.g. recrystallization.

The compounds of formula (II) are prepared by the following reaction scheme:

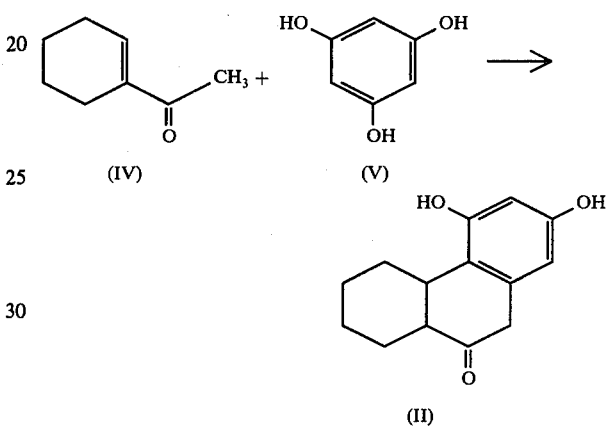

The compounds of formula (II) are prepared by treating 1-acetylcyclohexene (IV) with phloroglucinol (V) under an inert atmosphere such as argon, neon, nitrogen and the like, preferably nitrogen in the presence of both a strong base and an alcoholic solvent. Although the particular strong base employed is not critical, it is preferred that the reaction be run in the presence of an alkali metal hydroxide such as potassium hydroxide, sodium hydroxide and the like, an alkali metal alkoxide, such as sodium methoxide, potassium methoxide, sodium ethoxide and the like, or an alkali metal hydride such as sodium hydride, potassium hydride and the like, preferably potassium hydroxide. The particular solvent employed is critical and must be an alcoholic solvent such as an alkoxy alcohol, e.g., 2-methoxyethanol, 2-ethoxyethanol and the like, a lower alkanol such as methanol, ethanol, propanol, n-butanol and the like, or an ether of ethylene glycol such as methylether or ethylether, preferably 2-methoxyethanol. The temperature of the reaction is not critical, but it is preferred that the reaction be run at temperatures from about 50 to 150° C., especially the reflux temperature of the solvent. The reaction is run from 1 to 40 hours, preferably 3 to 6 hours. The compounds of formula (II) are recovered using conventional techniques, e.g. acidification followed by recrystallization.

The compounds of formulae (IV) and (V) are known and may be prepared by methods disclosed in the literature.

The compounds of formula (I') are useful because they possess pharmacological activity in animals as hypolipidemic agents, as indicated by the fall of cholesterol and triglyceride levels in male albino Wistar rats weighing 110 to 130 g. initially. The rats are maintained on drug-free laboratory chow diets for seven days and then divided into groups of 8 to 10 animals. Each group, with the exeception of the control, is then given orally 30 milligrams per kilogram of body weight per diem of the compound for six days. At the end of this period, the animals are anethetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium Mediad Inc., New York, [345–347]) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I') may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of compounds (I') employed in the alleviation of lipidemia may vary depending on the particular compound employed and the severity of the condition being treated. However, in general, satisfactory results are obtained when the compounds of formula (I') are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 3000 milligrams. Dosage forms suitable for internal use comprise from about 75 to 1500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
| --- | --- |
| 2,4-dimethoxy-4b,5,6,7,8,8a,9,10-octahydro-9-oxo-phenanthrene | 150 |
| inert solid diluent (starch, lactose, kaolin). | 300 |

EXAMPLE I

2,4-Dihydroxy-4b,5,6,7,8,8a,9,10-octahydro-9-oxo-phenanthrene

To a flask equipped with a stirrer, dropping funnel, condenser and gas inlet tube maintained under a nitrogen atmosphere, there is added 50 g. (0.89) moles of potassium hydroxide in one liter of 2-methoxyethanol. Stirring is initiated and 100 g. (0.79 mole) of anhydrous phloroglucinol is added in three portions, followed by the addition of 100 g. (0.80 mole) of 1-acetyl-cyclohexene while maintaining the temperature at 50° C. The resulting solution is refluxed at 140° C. for 4 hours. After cooling there is then added gradually 53.6 g. of acetic acid while obtaining a pH of approximately 7. The solvent is then removed in vacuo, and the residue is further heated in an oil bath at 70° C., to obtain a viscous residue. The resulting residue is dissolved in ethyl acetate and water washed twice with water, dried over anhydrous sodium sulfate, filtered and evaporated in vacuo to obtain a brown solid. The resulting solid is recrystallized from ethyl acetate/cyclohexane to give 2,4-dihydroxy-4b,5,6,7,8,8a,9,10-octahydro-9-oxo-phenanthrene; m.p. 220°–223° C.

EXAMPLE II

2,4-Dimethoxy-4b,5,6,7,8,8a,9,10-octahydro-9-oxo-phenanthrene

To a flask equipped with a stirrer, dropping funnel, condenser, and gas inlet tube maintained under a nitrogen atmosphere, there is added 23.2 g. (0.1 mole) of 2,4-dihydroxy-4b,5,6,7,8,8a,9,10-octahydro-9-oxo-phenanthrene, 20 g. (0.15 mole) of dimethyl sulfate, 22 g. (0.16 mole) of dry potassium carbonate and 500 ml. of dry acetone, the resulting mixture is then refluxed with stirring overnight. The resulting suspension is cooled, 5 ml. of water is added and stirring is continued for an additional 5 minutes. The mixture is filtered, and the filtrate is concentrated to dryness. The resulting residue is recrystallized from acetone/methanol to give 2,4-dimethoxy-4b,5,6,7,8,8a,9,10-octahydro-9-oxo-phenanthrene; m.p. 130°–131° C.

What is claimed is:

1. A compound of the formula

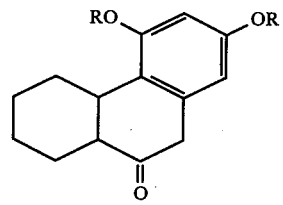

where R represents hydrogen or lower alkyl having 1 to 4 carbon atoms.

2. The compound of claim 1 which is 2,4-dihydroxy-4b,5,6,7,8,8a,9,10-octahydro-9-oxo-phenanthrene.

3. The compound of claim 1 which is 2,4-dimethoxy-4b,5,6,7,8,8a,9,10-octahydro-9-oxo-phenanthrene.

4. A pharmaceutical composition for use in the treatment of lipidemia which comprises a hypolipidemically effective amount of a compound of claim 1 and a pharmaceutically acceptable diluent or carrier therefor.

5. A method of treating lipidemia which comprises administering to a mammal in need of said treatment of hypolipidemic effective amount of a compound of claim 1.

* * * * *